(12) United States Patent
Paschke et al.

(10) Patent No.: US 7,614,878 B2
(45) Date of Patent: Nov. 10, 2009

(54) SYSTEM AND METHOD FOR DYNAMIC CONTROL OF ULTRASONIC MAGNETOSTRICTIVE DENTAL SCALER

(75) Inventors: Richard Paschke, Lutherville Timonium, MD (US); Noel S. Paschke, Lutherville Timonium, MD (US); Emery S. Rose, Manhasset, NY (US)

(73) Assignee: PCG, Inc., Lutherville Timonium, MD (US)

( * ) Notice: Subject to any disclaimer, the term of this patent is extended or adjusted under 35 U.S.C. 154(b) by 354 days.

(21) Appl. No.: 11/436,784

(22) Filed: May 18, 2006

(65) Prior Publication Data

US 2006/0269900 A1 Nov. 30, 2006

Related U.S. Application Data

(60) Provisional application No. 60/682,128, filed on May 18, 2005.

(51) Int. Cl.
*A61C 1/07* (2006.01)
(52) U.S. Cl. .................. 433/119; 310/316.01; 600/512
(58) Field of Classification Search .................. 310/26, 310/316.01; 433/119
See application file for complete search history.

(56) References Cited

U.S. PATENT DOCUMENTS

| | | | |
|---|---|---|---|
| 3,727,112 A | 4/1973 | Popescu | |
| 4,184,092 A | 1/1980 | Wieser | |
| 4,820,152 A * | 4/1989 | Warrin et al. | 433/86 |
| 4,965,532 A | 10/1990 | Sakurai | |
| 4,973,876 A | 11/1990 | Roberts | |
| 5,425,704 A | 6/1995 | Sakurai et al. | |
| 5,451,161 A | 9/1995 | Sharp | |
| 5,733,281 A | 3/1998 | Nardella | |
| 5,739,724 A | 4/1998 | Alexandre et al. | |
| 5,754,016 A * | 5/1998 | Jovanovic et al. | 318/118 |
| 5,819,027 A | 10/1998 | Budelman et al. | |

(Continued)

FOREIGN PATENT DOCUMENTS

WO WO85/02106 5/1985

OTHER PUBLICATIONS

International Search Report PCT/US06/19201, dated Jul. 11, 2007.

*Primary Examiner*—Walter Benson
*Assistant Examiner*—Bryan P Gordon
(74) *Attorney, Agent, or Firm*—Carter, DeLuca, Farrell & Schmidt, LLP

(57) ABSTRACT

A magnetostrictive ultrasonic dental scaler is disclosed. The magnetostrictive device comprises an oscillator adapted to provide electrical energy including a current and a voltage signal, a handpiece having a tool tip which vibrates in response to the electrical energy supplied to the handpiece and a control circuit. The control circuit includes a phase detector adapted to detect phase between current and voltage signals and to generate a phase detection signal as a function of the phase. The control circuit also includes a digital signal processor operatively connected to the phase detector. The digital signal processor adapted to process the phase detection signal through a digital loop filter to generate an error signal. The control circuit further includes a voltage controlled oscillator operatively connected to the digital signal processor, wherein the error signal outputs a voltage to operate the voltage controlled oscillator which in response thereto adjusts at least one of frequency and amplitude of vibrations of the tool tip.

19 Claims, 1 Drawing Sheet

U.S. PATENT DOCUMENTS

| | | |
|---|---|---|
| 5,880,580 A | 3/1999 | Johansen |
| 5,884,350 A * | 3/1999 | Kurze .......................... 5/600 |
| 5,897,569 A | 4/1999 | Kellogg et al. |
| 5,938,677 A * | 8/1999 | Boukhny et al. ............ 606/169 |
| 5,959,390 A | 9/1999 | Boukhny |
| 6,019,775 A | 2/2000 | Sakurai |
| 6,028,387 A | 2/2000 | Boukhny |
| 6,175,180 B1 | 1/2001 | Angelini et al. |
| 6,190,167 B1 * | 2/2001 | Sharp ......................... 433/119 |
| 6,241,520 B1 | 6/2001 | Gofman et al. |
| 6,503,081 B1 | 1/2003 | Feine |
| 6,545,390 B1 | 4/2003 | Hahn et al. |
| 6,577,642 B1 | 6/2003 | Fijolek et al. |
| 6,819,027 B2 | 11/2004 | Saraf |
| 2003/0222535 A1 | 12/2003 | Gofman et al. |

* cited by examiner

SYSTEM AND METHOD FOR DYNAMIC CONTROL OF ULTRASONIC MAGNETOSTRICTIVE DENTAL SCALER

PRIORITY CLAIM

The present application claims priority to a U.S. Provisional Application Ser. No. 60/682,128 entitled "Operational Description of a New Ultrasonic Magnetostrictive Dental Scaler" filed by Richard Pachke et al. on May 18, 2005.

BACKGROUND

1. Technical Field

The present disclosure relates to a system and method for dynamically controlling frequency and amplitude settings of an ultrasonic magnetostrictive dental scaler. More particularly, the present disclosure relates to a system and method for utilizing digital filter control loops to individually adjust amplitude and frequency of the vibrations.

2. Background of Related Art

Ultrasonic dental scalers are generally used to clean various types of build up from teeth. Dental scalers include a control circuit, a handpiece having an ultrasonic transducer, an energizing coil and a tool tip. In particular, the energizing coil actuates the transducer which then produces vibrational motion. The vibrational motion is then transformed into lateral motion of the dental scaler tool tip, which is typically elliptical. Vibration of the tool tip is controlled and, if required, adjusted during operation to tune the frequency and amplitude to desired operational frequency and amplitude. As operational conditions change, such as temperature, density of the material being removed, etc., operational frequency and amplitude change accordingly. Manual tuning of the dental scaler is inconvenient, therefore, automatic frequency and amplitude tuning circuits have been developed. More specifically, automatic tuning circuits utilizing feedback coils have been proposed. See, e.g., U.S. Pat. Nos. 5,451,161 and 6,241,520. However, these circuits suffer from a number of mechanical disadvantages (e.g., interconnection of additional wires, fragile wirings, placement of controls, etc.) and electronic disadvantages (e.g., inaccurate signal processing, interference, etc.). Therefore there is a need for an ultrasonic magnetostrictive dental scaler with improved control circuitry.

SUMMARY

The present disclosure relates to a magnetostrictive ultrasonic dental scaler which includes a handpiece and dental scaler device having a control circuit which dynamically maintains a desired operating point under varying loads and operating conditions. The operating point may be directly on a resonance of the handpiece at a fixed frequency shift from the resonance. The control circuit enables a greater level of control and enhanced performance by use of dynamic tracking of resonance under variable loading. In particular, the control circuit includes a digital signal processor which processes sensed feedback signals regarding frequency and amplitude of vibrations and filters the signals through dynamic filter loops to obtain error and/or control signals to adjust the output of the dental scaler thereby controlling the frequency and amplitude of vibrations and arriving at the desired operating point.

According to one aspect of the present disclosure, a magnetostrictive ultrasonic dental scaler is disclosed. The magnetostrictive dental scaler comprises an oscillator adapted to provide electrical energy including a current and a voltage signal, a handpiece having a tool tip which vibrates in response to the electrical energy supplied to the handpiece and a control circuit. The control circuit includes a phase detector adapted to detect phase between current and voltage signals and to generate a phase detection signal as a function of the phase. The control circuit also includes a digital signal processor operatively connected to the phase detector. The digital signal processor adapted to process the phase detection signal through a digital loop filter to generate an error signal. The control circuit further includes a voltage controlled oscillator operatively connected to the digital signal processor, wherein the error signal outputs a voltage to operate the voltage controlled oscillator which, in response thereto, adjusts at least one of frequency and amplitude of vibrations of the tool tip.

According to another aspect of the present disclosure, a control circuit for controlling a magnetostrictive ultrasonic dental scaler having a tool tip is disclosed. The control circuit includes a phase detector adapted to detect phase between current and voltage signals and to generate a phase detection signal as a function of the phase. The control circuit also includes a digital signal processor operatively connected to the phase detector. The digital signal processor adapted to process the phase detection signal through a digital loop filter to generate an error signal. The control circuit further includes a voltage controlled oscillator operatively connected to the digital signal processor, wherein the error signal outputs a voltage to operate the voltage controlled oscillator which in response thereto adjusts at least one of frequency and amplitude of vibrations of the tool tip.

According to a further aspect of the present disclosure, a magnetostrictive ultrasonic dental scaler is disclosed. The magnetostrictive dental scaler comprises an oscillator adapted to provide electrical energy including a current and a voltage signal, a handpiece having a tool tip which vibrates in response to the electrical energy supplied to the handpiece and a control circuit adapted for dynamically controlling the oscillator and the handpiece. The dental scaler also includes a voice input control module adapted to receive oral input commands and to output acknowledging responses thereto. The oral input commands are adapted to control activation, mode, power, and adjustment functions of the magnetostrictive ultrasonic dental scaler.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Figure 1:
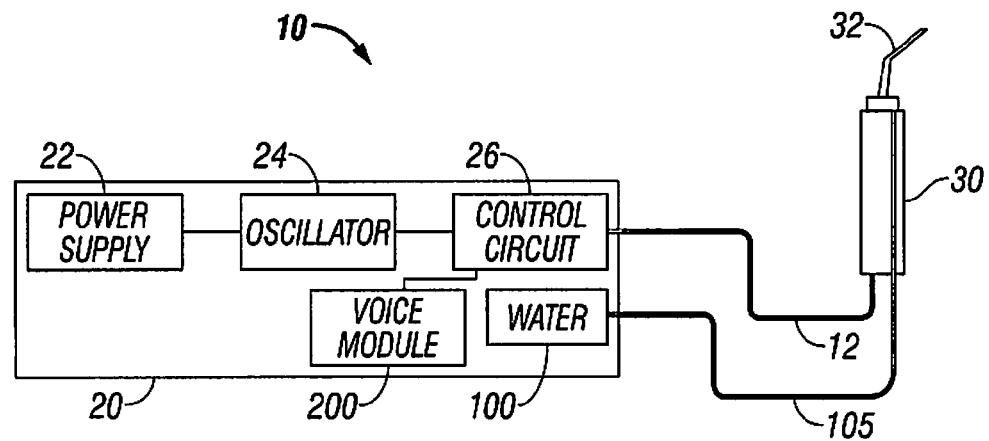
FIG. 1 is a schematic diagram of an ultrasonic dental scaler according to the present disclosure.

FIG. 1 shows a dental scaler system 10 including a dental scaler device 20 and a handpiece 30 connected to the scaler device 20 via a cable 12. The dental scaler device 20 includes a DC power supply 22, which may be either internal or external to the scaler device 20, an oscillator 24, and a control circuit 26. The DC power supply 22 provides voltage to the scaler device 20. This voltage is used to provide functionality to the scaler device 20 (e.g., indicator lights, switches, etc.) and to power the oscillator 24 which converts DC voltage into high frequency signals for energizing the handpiece 30.

The handpiece 30 includes a tip 32 and an energizing coil 34 which ultrasonically vibrates the tool tip 32. The tool tip 32 may be either a fixed or a modularly removable tool. The tool tip 32 is brought into contact with teeth during scaling procedures wherein vibration of the tool tip 32 dislodges buildup. The handpiece 30 includes an irrigation system that supplies a liquid (e.g., water) to wash away debris as well as cool the tool tip 32.

Figure 2:
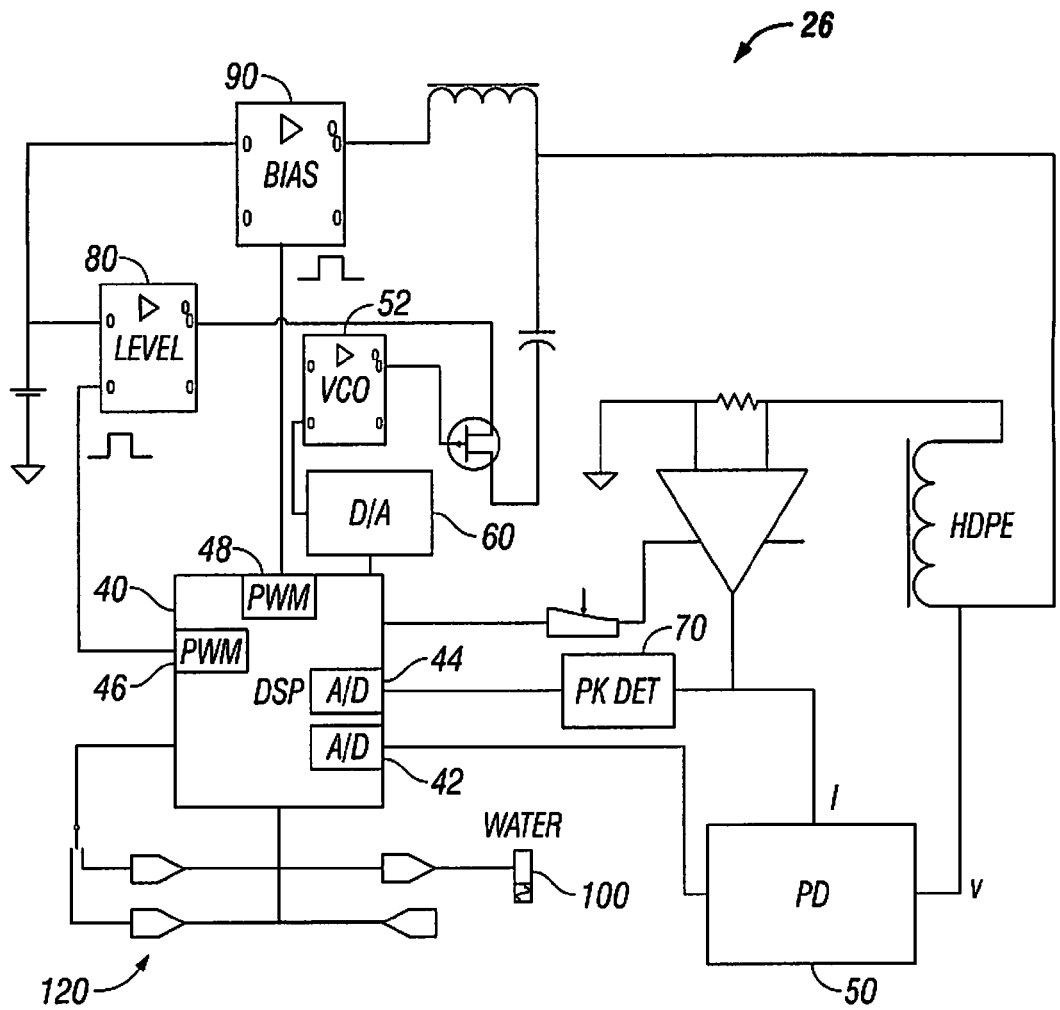
FIG. 2 is a schematic diagram of a control circuit according to the present disclosure.

The control circuit 26 controls the frequency and amplitude of the vibrations produced by the scaler device 20. In particular, the control circuit 26 includes a frequency and an amplitude adaptive control loops which dynamically adjust the respective ultrasonic properties. The control loops are implemented using the components shown in greater detail in FIG. 2. The control circuit 26 includes a digital signal processor (DSP) 40 which operates an adaptive digital loop filter for both the frequency and amplitude control loops. The DSP 40 may be either a TMS320C42XX or TMS320C28XX series processor manufactured by Texas Instruments, Inc. of Dallas, Tex. or a similar signal processor. The DSP 40 may also be a microprocessor or any other programmable digital device. Further, the DSP 40 may include memory which may be either non-volatile memory or volatile memory for permanent or temporary storage of data.

The frequency control loop is implemented in the following manner: the DSP 40 is operatively connected to a phase detector (PD) 50 which detects phase between the current and voltage signals and transmits the phase signal to the DSP 40. The PD 50 is part of a phase lock loop (PLL) device such as a Signetics 4046 PLL device available from Signetics High Technology, Inc. of San Jose, Calif. The PLL device includes the PD 50, a voltage controlled oscillator (VCO) 52, and an amplifier.

The DSP 40 includes an offset algorithm which asserts a change in the operating point (e.g., frequency, phase, etc.) to accommodate situations where an initial operation point of the handpiece 30 produces feedback. After a user command for off resonance operation is detected by the DSP 40, the offset algorithm detects feedback by varying the operating point and analyzing the response in amplitude. The DSP 40 tracks the operating point to maintain the operating point at a predetermined offset from resonance under varying load. Namely, the DSP 40 continues to make adjustments until an optimal operating point is reached.

Further, the DSP 40 includes an adaptive algorithm which automatically adjusts loop filter parameters to maximize the performance of various types of handpieces and tool tips. Start-up transients are monitored and optimized for overshoot and settling time by means of loop filter parameter adjustment. The adaptive algorithm detects amplitude via the peak detector 70 and transmits the amplitude signal to the DSP 40 where the amplitude signal is stored. After the ultrasound vibrations are stopped (e.g., oscillator 24 is turned off) the amplitude signal is analyzed to determine if the amplitude signals exceed a predetermined amplitude threshold. If the amplitude signal exceeds the amplitude threshold, then the digital loop filter gain is decreased to ensure that during subsequent operation, the amplitude is lowered.

The DSP 40 receives the peak current and phase signals from the PD 50 at a first analog-to-digital converter (A/D) 42. The DSP 40 vectorially subtracts a known vector component caused by static inductance (Lo) of the handpiece 30 from the phase signal to obtain a frequency motional feedback signal which is reflective of actual motion.

The DSP 40 also calculates an error signal which is transmitted to the VCO 52 through a digital-to-analog converter (D/A) 60. The error signal outputs a voltage which operates the VCO 52. The DSP 40 includes an adaptive loop filter which may be implemented as an algorithm (e.g., software, firmware, etc.) to calculate the error signal. This process dynamically maintains the desired operating point of the handpiece 30 under varying loads. The operating point may be directly on a resonance of the handpiece 30 and/or the tool tip 32 or the operating point may be at fixed frequency shift from the resonance which enables a better control over a lower amplitude of vibration. The frequency shift may be a fixed frequency offset (e.g., user-defined) or a dynamically varying frequency offset determined by the load applied to the tool tip 32.

Error conditions such as failure of the PLL device to acquire or maintain lock can be monitored and compensated for by using corrective algorithms. These algorithms can adjust start up or loop parameters until required performance is achieved.

The control circuit 26 also maintains amplitude of vibration under varying loads by sensing the motional component of current and responding to changes in the load by varying the output power. This is accomplished by using a pulse width modulation peripheral 46 which controls a voltage level circuit 80 driving the current through the handpiece 30. A second A/D 44 senses current from a peak detector (PK DET) 70. The DSP 40 processes the current signal through a second adaptive loop filter which may be implemented as either software or firmware. The DSP 40 separates the motional component of current, which represents the mechanical amplitude of vibration, from the static inductance component by vectorial subtraction thereof to obtain an amplitude motional feedback signal which is reflective of actual motion. The DSP 40 thereafter adjusts the PWM duty cycle at the PWM peripheral 46 to maintain a constant amplitude of vibration under varying load.

DC bias is used to drive the handpiece 30 and tool tip 32 in a linear portion of its operating curve. For optimum efficiency, it is important to prevent current from flowing in a reverse direction. Conventional devices maintained DC bias at a fixed level regardless of vibrational amplitude or as a fixed function thereof. Consequently, DC bias was optimal only at a predetermined amplitude of vibration. The present disclosure provides for a method of dynamically adjusting DC bias in addition to frequency and amplitude. This is accomplished by using PWM control. The DSP 40 controls the bias current via a bias control algorithm, wherein a PWM peripheral 48 controls a bias amplifier (BIAS) 90. The DSP 40 monitors current and detects a negative cross of the current using the peak detector 70. Upon detecting a negative cross, the DSP 40 controls bias to achieve maximum electromechanical coupling efficiency between the handpiece 30 and the tool tip 32.

It is also contemplated that the scaler device 20 and the handpiece 30 may include an irrigation system which includes a liquid dispenser 100 and one or more hoses 105 supplying the liquid to the treatment site. The hoses 105 pass through the handpiece 30. The temperature of the liquid may be adjusted during application. In particular, the temperature of the liquid may be adjusted by varying the DC bias so that the current passing through the handpiece 30 is used to heat the water.

The scaler device 20 and the handpiece 30 may be controlled via a variety of input devices, such as foot switches, hand switches disposed either on the scaler device 20 and/or the handpiece 30. Inputs and output ports (I/O) 120 are connected to the DSP 40 and allow for the user to control the operation of the dental scaler. The input devices are connected to the I/O 120. Although foot and hand switches are commonly used these input devices are limited to a single or a double switching function, which requires addition of rheostat to control power making the device even more cumbersome. Use of radio controlled switches eliminates a cable connection to the system but does not significantly improve control of the system. The present disclosure provides a novel voice input control module 200 as shown in FIG. 1. The voice module 200 provides on-off functionality as well as facilitates complete control of other features of the dental scaler 30 thereby allowing for operation of the device without being distracted from treatment by reaching for controls.

The voice module 200 is a bi-directional transducer that allows input of commands and provides audio feedback in response thereto (e.g., acknowledgment). The input commands may be unambiguous one to three syllable words. These commands may include the following: activation commands (e.g., "on," "off"), mode (e.g., "perio," "endo," "scale," "audio"), power (e.g., "max," "mid," "low," "up," "down"), adjustment control (e.g., "boost," "zero," "1," "2," "3," "4," "5," "level," "reset"). The mode commands set the operational output power range of the device. The perio mode designates the lowest power or stroke output to accommodate patient sensitivity and optimize activation of thinner tool tips 32. The endo mode optimizes the stroke range consistent with activating endo files to maximize debridement and minimize breakage. The scale mode provides the broadest range that includes low levels for patient sensitivity as well as high power for removing tenacious buildup. All control and power commands are designed to respond proportionally to the selected mode. The "level" command recalls the current setting and states the currently selected mode and power level. Audio "1-5" commands set the level of the output audio. The "reset" command sets all control to preset conditions (e.g., mode is set to scale, power is set to low, boost is set to zero, and audio level is set to 2).

Those skilled in the art will recognize that the circuits and methods disclosed herein can be easily adapted to other types of electromechanical transducer systems, e.g., piezoceramic systems.

While several embodiments of the disclosure are shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A magnetostrictive ultrasonic dental scaler comprising:
   an oscillator adapted to provide electrical signals including a current and a voltage signal;
   a handpiece having a tool tip which vibrates in response to the electrical signals supplied to the handpiece; and
   a control circuit comprising:
   a phase detector adapted to detect phase between current and voltage signals and to generate a phase detection signal as a function of the phase;
   a digital signal processor operatively connected to the phase detector, the digital signal processor configured to process the phase detection signal through a digital loop filter to generate an error signal, wherein the digital signal processor is further configured to vectorially subtract a known vector component caused by static inductance of the handpiece to obtain a frequency motional feedback signal reflective of actual motion; and
   a voltage controlled oscillator operatively connected to the digital signal processor, wherein the digital signal processor outputs a voltage control signal as a function of the error signal and the frequency motional feedback signal to operate the voltage controlled oscillator which in response thereto adjusts at least one of frequency and amplitude of vibrations of the tool tip.

2. A magnetostrictive ultrasonic dental scaler as in claim 1, wherein the voltage controlled oscillator adjusts at least one of frequency and amplitude to maintain a preferred operating point under varying loads and operating conditions.

3. A magnetostrictive ultrasonic dental scaler as in claim 2, wherein the preferred operating point is frequency of resonance.

4. A magnetostrictive ultrasonic dental scaler as in claim 2, wherein the preferred operating point is a fixed frequency offset from frequency of resonance.

5. A magnetostrictive ultrasonic dental scaler as in claim 2, wherein the preferred operating point is a dynamically varying frequency offset from frequency of resonance, the dynamically varying frequency offset being determined by the load applied to the tool tip.

6. A magnetostrictive ultrasonic dental scaler as in claim 1, further comprising:
   a peak detector operatively connected to the digital signal processor, the peak detector adapted to detect current; and
   a pulse width modulation peripheral which controls a voltage level circuit adapted to drive the handpiece.

7. A magnetostrictive ultrasonic dental scaler as in claim 1, wherein the digital signal processor is configured to independently control DC bias to optimize electro-mechanical coupling of the handpiece and the tool tip at any frequency and any amplitude of vibrations of the tool tip.

8. A magnetostrictive ultrasonic dental scaler as in claim 1, further comprising:
   an irrigation system including a liquid dispenser and at least one hose adapted to supply the liquid from the liquid dispenser to the handpiece; wherein the digital signal processor is configured to independently control DC bias to adjust temperature of the liquid.

9. A magnetostrictive ultrasonic dental scaler as in claim 1, further comprising:
   a voice input control module adapted to receive oral input commands and to output acknowledging responses thereto.

10. A magnetostrictive ultrasonic dental scaler as in claim 7, wherein the oral input commands are adapted to control at least one of activation, mode, power, and adjustment functions of the magnetostrictive ultrasonic dental scaler.

11. A control circuit for controlling a magnetostrictive ultrasonic dental scaler having a tool tip, the control circuit comprising:
   a phase detector adapted to detect phase between current and voltage signals and to generate a phase detection signal as a function of the phase;
   a digital signal processor operatively connected to the phase detector, the digital signal processor configured to process the phase detection signal through a digital loop filter to generate an error signal, wherein the digital signal processor is further configured to vectorially subtract a known vector component caused by static inductance of the handpiece to obtain a frequency motional feedback signal reflective of actual motion; and a voltage controlled oscillator operatively connected to the digital signal processor, wherein the digital signal processor outputs a voltage control signal as a function of the error signal and the frequency motional feedback signal to operate the voltage controlled oscillator which in response thereto adjusts at least one of frequency and amplitude of vibrations of the tool tip.

12. A control circuit as in claim 11, wherein the voltage controlled oscillator adjusts at least one of frequency and amplitude to maintain a preferred operating point under varying loads and operating conditions.

13. A control circuit as in claim 11, wherein the preferred operating point is frequency of resonance of the tool tip.

14. A control circuit as in claim 12, wherein the preferred operating point is a frequency offset from frequency of resonance.

15. A control circuit as in claim 11, further comprising:
a peak detector operatively connected to the digital signal processor, the peak detector adapted to detect current; and
a pulse width modulation peripheral which controls a voltage level circuit adapted to drive the handpiece.

16. A control circuit as in claim 11, wherein the peak detector detects at least one amplitude signal and transmits the at least one amplitude signal to the digital signal processor, wherein the digital signal processor decreases gain of the digital loop filter if the at least one amplitude signal exceeds a predetermined amplitude threshold.

17. A control circuit as in claim 11, further comprising:
a voice input control module adapted to receive oral input commands and to output acknowledging responses thereto.

18. A control circuit as in claim 17, wherein the oral input commands are adapted to control at least one of activation, mode, power, and adjustment functions of the magnetostrictive ultrasonic dental scaler.

19. A magnetostrictive ultrasonic dental scaler comprising:
an oscillator adapted to provide electrical signals including a current and a voltage signal;
a handpiece having a tool tip which vibrates in response to the electrical signals supplied to the handpiece;
a control circuit adapted for dynamically controlling the oscillator and the handpiece, the control circuit including:
a phase detector adapted to detect phase between current and voltage signals and to generate a phase detection signal as a function of the phase;
a digital signal processor operatively connected to the phase detector, the digital signal processor configured to process the phase detection signal through a digital loop filter to generate an error signal, wherein the digital signal processor is further configured to vectorially subtract a known vector component caused by static inductance of the handpiece to obtain a frequency motional feedback signal reflective of actual motion; and
a voltage controlled oscillator operatively connected to the digital signal processor, wherein the digital signal processor outputs a voltage control signal as a function of the error signal and the frequency motional feedback signal to operate the voltage controlled oscillator which in response thereto adjusts at least one of frequency and amplitude of vibrations of the tool tip; and
a voice input control module adapted to receive oral input commands and to output acknowledging responses thereto, wherein the oral input commands are adapted to control at least one of activation, mode, power, and adjustment functions of the magnetostrictive ultrasonic dental scaler.

* * * * *

UNITED STATES PATENT AND TRADEMARK OFFICE
CERTIFICATE OF CORRECTION

PATENT NO. : 7,614,878 B2 Page 1 of 1
APPLICATION NO. : 11/436784
DATED : November 10, 2009
INVENTOR(S) : Paschke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 530 days.

Signed and Sealed this

Nineteenth Day of October, 2010

David J. Kappos
*Director of the United States Patent and Trademark Office*